United States Patent [19]
Johnson et al.

[11] Patent Number: 5,980,526
[45] Date of Patent: Nov. 9, 1999

[54] WEDGE OSTEOTOMY DEVICE INCLUDING A GUIDE FOR CONTROLLING OSTEOTOMY DEPTH

[75] Inventors: Wesley Johnson, Menomonie; William B. Smith, Mequon; Alan E. Edwards, Waukesha, all of Wis.

[73] Assignee: Orthopaedic Innovations, Inc., Golden Valley, Minn.

[21] Appl. No.: 08/799,606

[22] Filed: Feb. 12, 1997

[51] Int. Cl.⁶ ........................................................ A61F 5/00
[52] U.S. Cl. ................................. 606/86; 606/86; 606/87; 606/88; 606/89
[58] Field of Search .................................. 606/86, 87, 88, 606/89

[56] References Cited

U.S. PATENT DOCUMENTS

| | | |
|---|---|---|
| 4,335,715 | 6/1982 | Kirkley . |
| 4,349,018 | 9/1982 | Chambers . |
| 4,421,112 | 12/1983 | Mains et al. . |
| 4,565,191 | 1/1986 | Slocum . |
| 4,627,425 | 12/1986 | Reese . |
| 4,750,481 | 6/1988 | Reese . |
| 4,787,383 | 11/1988 | Kenna ......................................... 606/88 |
| 4,892,093 | 1/1990 | Zarnowski et al. ......................... 606/88 |
| 5,021,056 | 6/1991 | Hofmann et al. . |
| 5,053,039 | 10/1991 | Hofmann et al. . |
| 5,246,444 | 9/1993 | Schreiber . |
| 5,304,180 | 4/1994 | Slocum . |
| 5,474,559 | 12/1995 | Bertin et al. ............................... 606/88 |
| 5,486,178 | 1/1996 | Hodge ....................................... 606/88 |
| 5,540,695 | 7/1996 | Levy . |

OTHER PUBLICATIONS

Undated pages referencing Intermedics Orthopedics products—10 pages, believed to be available prior to the filing date of the present application.

*Primary Examiner*—Michael Buiz
*Assistant Examiner*—Tan-Uyen T. Ho
*Attorney, Agent, or Firm*—Gregory F. Cotterell

[57] ABSTRACT

The present invention encompasses a device for providing a wedge osteotomy comprising an osteotomy guide having a guide body that provides reference slots at specific angles to one another and which define planes, all of the planes meeting at a predetermined line of intersection. The slots are employed to properly position resection blocks, which are placed against the bony surface into which the osteotomy is to be cut. The resection blocks have saw blade guiding slots defining the desired planes in which cuts are to be made and which guide s surgical saw blade during a cutting operation. Through the use of a calibrated guide pin, the guide body is so oriented as to position the planes of the cuts so that they intersect at a predetermined line of intersection adjacent the medial surface of the tibia, thereby providing an uncut bone bridge of the desired width and orientation.

6 Claims, 5 Drawing Sheets

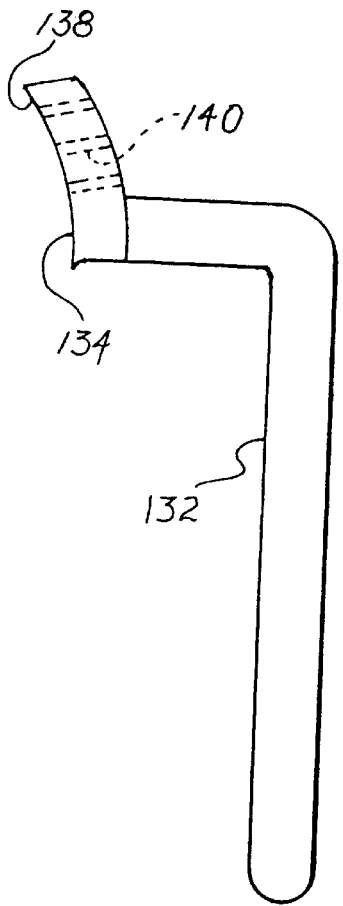
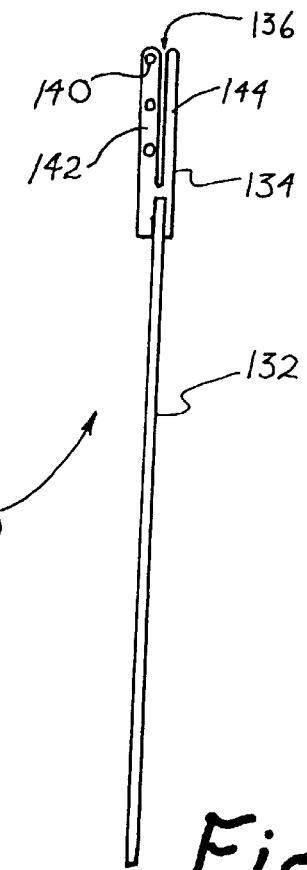
Fig. 3  Fig. 4
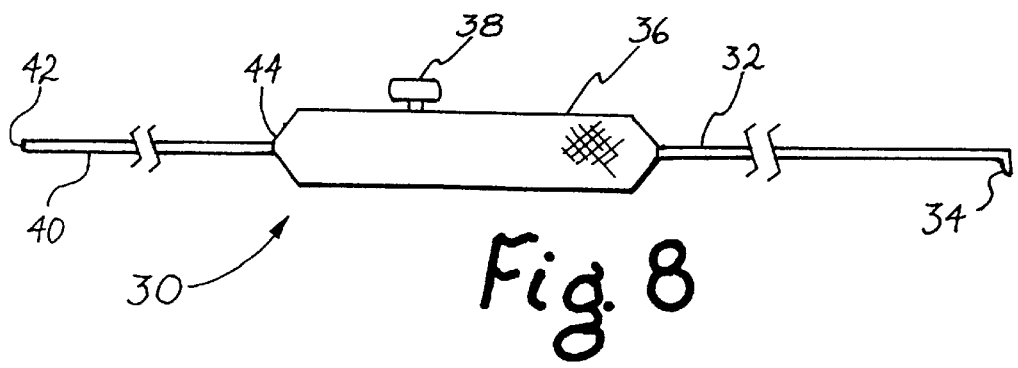
Fig. 8

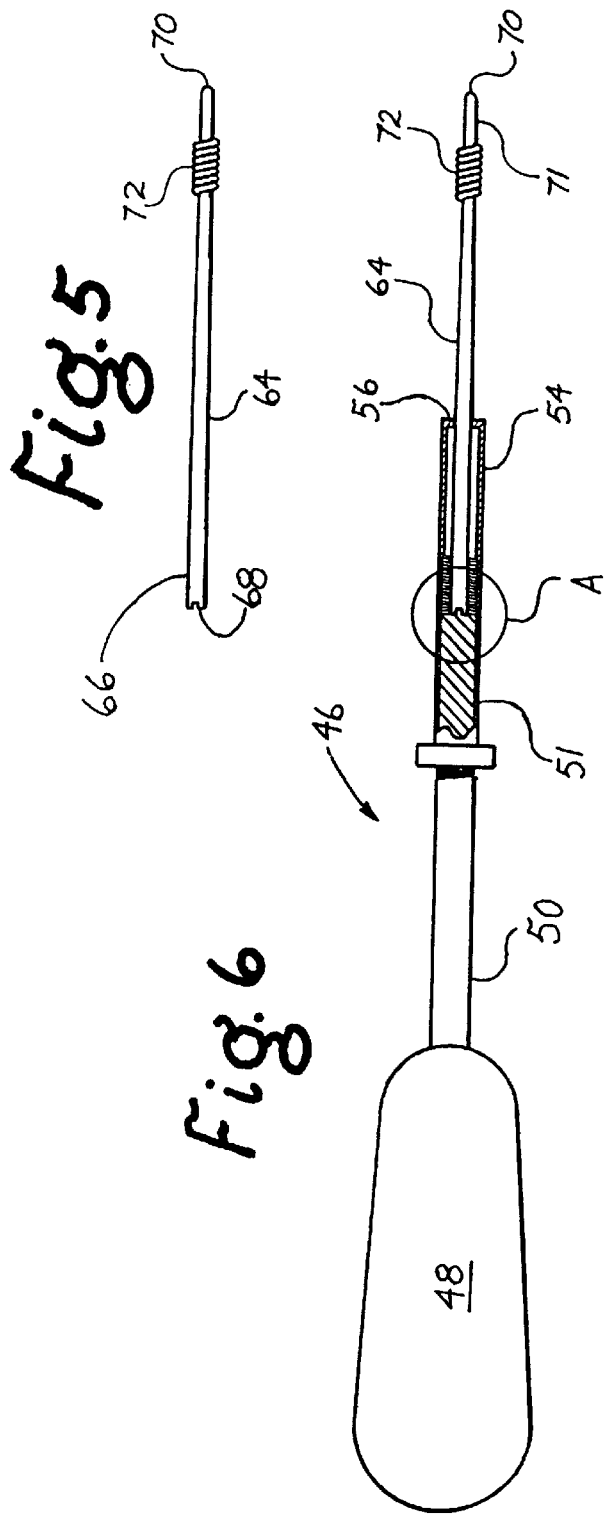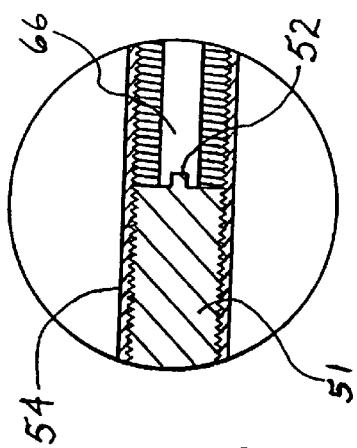

WEDGE OSTEOTOMY DEVICE INCLUDING A GUIDE FOR CONTROLLING OSTEOTOMY DEPTH

FIELD OF THE INVENTION

The present invention relates to devices and methods used to perform cuneiform osteotomy procedures on long bones, particularly in the upper tibial region.

BACKGROUND OF INVENTION

The articulation of the tibia and femur of a normal human knee joint is not perfectly straight, but is bent outward or away from the centerline of the body. This condition is known as valgus, with normal considered to be at approximately six degrees. This creates a mechanical axis extending from the head of the femur, through the center of the knee joint, to the center of the ankle joint. Assuming the mechanical axis of the leg is within normal parameters, the loading patterns on the leg, which can be great, will be properly distributed.

Several conditions can lead to an alteration of the normal mechanical axis of a leg. Degenerative osteoarthritis can sometimes cause a condition in long human bones which causes the bone to change shape. Instead of being relatively straight, the bone becomes curved or misshapen over a period of time. This can be either an outward direction (valgus), in an inward direction (varus), or compound shapes. Most frequently, the valgus or varus condition occurs below the articular surface of the tibia, affecting the load distribution on the knee joint. The result of this condition is that the mechanical axis of the leg becomes altered, with resultant load patterns that the knee joint cannot properly accomrnodate. Great pain and difficulty of movement can result, with a consequent restriction of lifestyle. A further problem associated with this condition is increased joint arthritis due to improper load distribution. In younger patients, improper bone growth can lead to similar problems, and require similar treatment. Examples of this condition are commonly known as bowleggedness (genu varum) ox knock knee (genu valgum).

Among the techniques developed tot dealing with valgus or varus conditions, one of the most successful is known as cuneiform or wedge osteotomy. Treatment requires that the angular deformity be determined by one of several methods. The desired correction angle is determined by adding the preoperative varus angle or valgus angle to the desired postoperative valgus angle. Generally, between five and thirteen degrees of valgus have been shown to result in the most successful outcome in osteotomy procedures.

In performing a cuneiform or wedge osteotomy, a wedge shaped section of bone is surgically removed to allow realignment of the bone. The wedge cut made by the surgeon should not completely sever the tibia, however. A bridge of residual bone should remain uncut, this portion serving in effect as a "hinge" for reduction of the wedge-shaped gap that remains following removal of the bone wedge. The depth of the wedge is critical in that if the wedge is too shallow, thus rendering the bridge too wide, the resulting wide fulcrum results in over stressing of the medial cortex during wedge compression, causing fracture of the bone bridge. If the wedge is too deep (the residual bone bridge is too narrow) the residual bone bridge, if not completely severed, lacks significant strength to provide medial stability to the reduced osteotomy. Reduction of the wedge-shaped gap allows realignment of the bone, and correction of the loading patterns of the leg. Bone plates will be installed to secure the reshaped bone, at least through the healing process.

Several types of devices have been developed to assist the surgeon in carrying out the osteotomy process. One type of device comprises a sequence of jigs which are affixed to the tibia in a position determined by the surgeon. This requires the drilling of holes in the tibia to anchor the jigs. A first jig contains a single slot through which the surgeon inserts the blade of an oscillating bone saw and makes a first cut. The first jig is removed and a second jig containing a series of slots corresponding to different angles is then affixed to the same position as the first jig. The surgeon inserts the oscillating bone saw blade into the desired slot and makes a second cut. The second cut should terminate at the same point as the first cut, creating a clean apex. Ideally, this allows a section of bone to remain integrated. Careful compression of the resected area reshapes the bone, and is secured by the placement of an osteotomy bone plate.

Problems in using jig based devices include the possibility of inaccurate estimation of the resection surfaces, resulting in an insufficient area of residual bone, or even of a severing of the upper part of the tibia. Also, the two cuts may not be aligned properly, resulting in an unclean cut which could interfere with the compression and mating process, and also affect the healing process. By their nature, jigs are rigid devices which are unable to adjust to the varied contours of an individual patient's anatomy. Thus, using such devices is often a compromise, and can lead to less than ideal results.

Other devices are also known which provide varying degrees of adjustability to allow the surgeon to select a predetermined desired angle. These devices typically require the surgeon to make an unaided first cut. The device includes a flat, blunt blade which is inserted into the first cut. The surgeon then adjusts the angle of the saw blade guide on the device to create a properly angled wedge to be excised from the bone. Problems with such devices include a lack of precision, with the possibility of locating the wedge apex too shallow or too deep and producing an improperly sized or angled wedge.

What is clearly needed, therefore, is a method and instrumentation for performing osteotomy procedures which allows greater accuracy and improved precision in determining the location of the resection surfaces. Also highly desirable would be a system allowing a greater degree of flexibility in positioning the device in a coronal plane or angle it away from the coronal plane. This would permit an osteotomy procedure to be biased in a posterior or anterior slope, if required. Finally, an osteototmy system permitting resectioning procedures on bones, other than the upper tibial region would be highly desirable.

SUMMARY OF INVENTION

The present invention comprises apparatus and methods allowing greater accuracy, increased precision and flexibility when performing osteotomy procedures. In one embodiment, the invention comprises an osteotomy guide having a guide body that provides reference slots at specific angles to one another and which define planes, all of the planes meeting at a predetermined line of intersection. The slots are employed to properly position resection blocks which are placed against the bony surface into which the osteotomy is to be cut. The resection blocks have saw blade guiding slots defining the desired planes in which cuts are to be made and which guide a surgical saw blade during a cutting operation. Through the use of a calibrated guide pin, the guide body is so oriented as to position the planes of the cuts so that they intersect at a predetermined line of intersection adjacent the medial surface of the tibia, thereby providing an uncut bone bridge of the desired width and orientation.

If desired, the resection blocks may move in a telescoping fashion to be brought into contact with the tibial surface. Preferably, however, the resection blocks have blade-shaped extension bars that are received in the desired reference slots of the guide block and, when the resection blocks are appropriately positioned against the tibia, are locked in their respective slots.

A procedure for a high tibial osteotomy is provided. First, the proximal tibia and joint capsule are exposed. The plane of the knee joint is determined and marked by the insertion of Keith pins. Following this, a drill guide is positioned against the lateral cortex of the proximal tibia and abutting the Keith pins. The drill guide is provided with a block having a chevron shaped surface configured to fit against the lateral surface of the tibia and capable of use with both right and left knees. A central hole in the drill guide body corresponds with an anterior screw hole in an L-shaped plate used to secure the completed osteotomy. A hole posterior to the central hole corresponds to the posterior screw hole in the L-Plate. The drill guide includes a portion extending into contact with a distal portion of the tibial shank and includes a drill guide hole for forming an anchor hole for securing the L-shaped reduction clamp when the osteotomy is closed. The drill guide is positioned to orient the L-Plate on the lateral tibia and to center the distal portion of the plate on the lateral tibial shaft. All three holes are drilled at this time. The posterior proximal hole is drilled completely through the width of the tibia. The anterior proximal hole is drilled midway through the tibia, and the distal anchor hole is drilled through one cortical wall.

An elongated depth gauge of predetermined length is passed through the posterior proximal drill hole and hooked to the medial cortex. The depth gauge includes a handle slidable along the length of the depth gauge, and the handle is advanced to the lateral cortical surface and is locked in place, thereby establishing a reference point for the medial cortex.

The length of the depth gauge extending distally from the handle through the tibia thus represents the width of the tibia. In this exemplary embodiment, one chooses a handle having a desired length along the length of the depth gauge such that the length of the depth gauge that extends proximally from the handle can be used to adjust the depth to which a calibrated guide pin will be received in the tibia. The proximal end of the depth gauge is placed into the barrel of a pin driver and the pin driver is adjusted to the length of the proximal end of the depth gauge. A calibrated guide pin is placed into the pin driver and is threaded into the posterior proximal drill hole.

As the calibrated guide pin is advanced, the collar of the pin driver contacts the lateral cortex. Further advancement of the guide pin will pull the guide pin from the pin driver. The positioning of the collar is such that when the guide pin dislodges from the pin driver, the length of the guide pin that protrudes from the drill hole will establish a reference point for the resection guide body. The protruding end of the guide pin received in an opening in the guide body, thereby positioning the guide body so that the resection planes will converge at a predetermined depth within the tibia, thereby positioning the apex of the wedge osteotomy at a desired distance from the medial cortex, typically 5 mm.

Appropriate slots in the guide body are chosen so that the resection planes will define the desired wedge angle. The osteotomy guide is placed over the calibrated guide pin and abutted against the distal end of the guide pin. The bar portions of two resection blocks are received in the selected slots, and the blocks are secured to the surface of the tibia by anchor pins, the bars being locked, if desired, in the guide body. Saw cuts are then made in the tibia through the use of the saw guides, the planes of the cuts intersecting in the predetermined line of intersection and leaving a bone bridge of the desired width. The osteotomy is gradually reduced with a reduction clamp, causing realignient of the bone, and an L-shaped plate referred to above is installed to secure closure of the osteotomy.

BRIEF DESCRIPTION OF THE DRAWINGS

FIG. 3 is a top view of a resection block for use with the guide body of FIG. 2;

FIG. 4 is a side view of the resection block of FIG. 3;

FIG. 5 is a side view of a calibrated guide pin;

FIG. 6 is side view in partial cross section of a pin driver of the invention with the guide pin of FIG. 5 received therewithin;

FIG. 6A is an enlarged view of the circled portion of FIG. 6;

FIG. 8 is a plan view of a depth gauge with adjustable handle.

DETAILED DESCRIPTION OF THE PREFERRED EMBODIMENT

Figure 1:
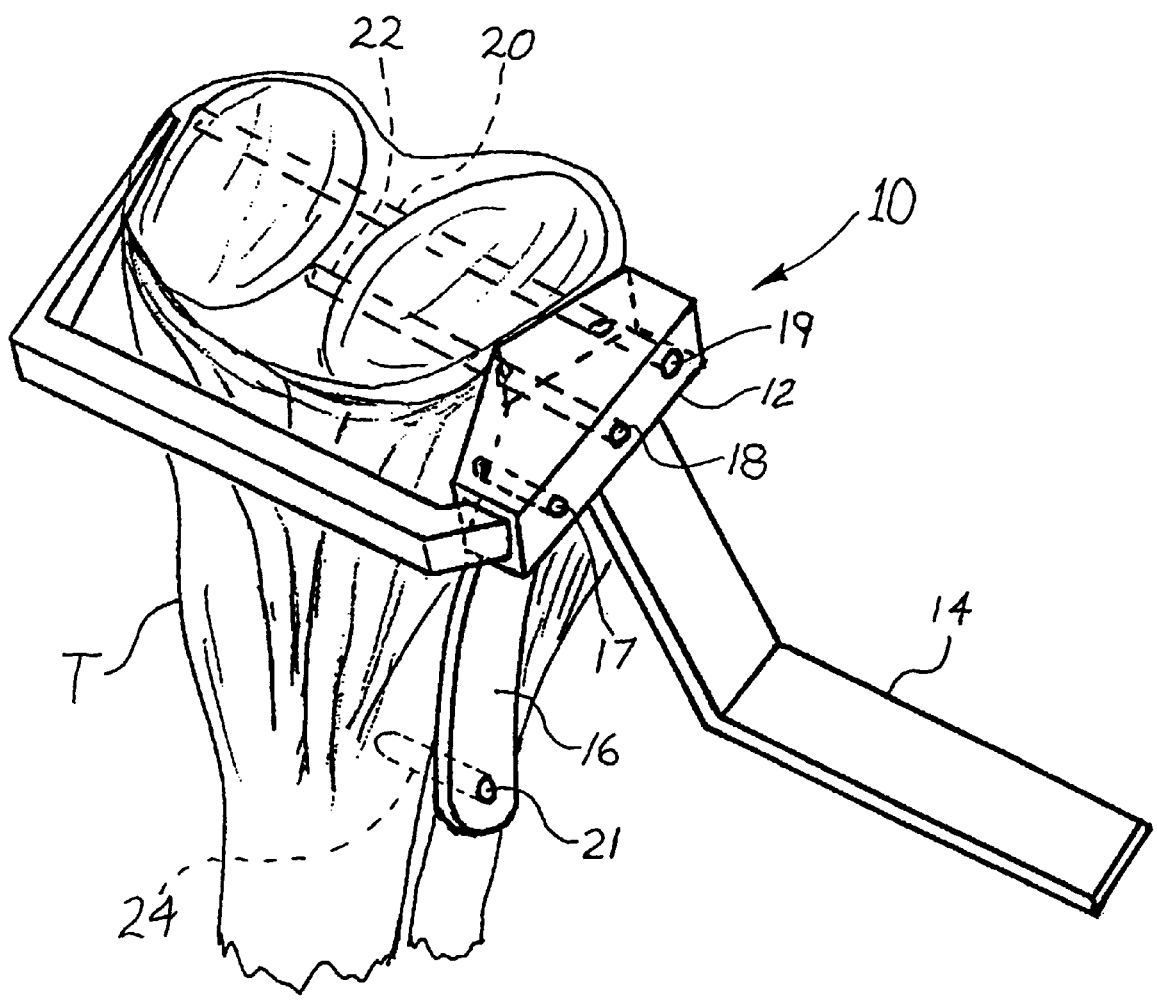
FIG. 1 is a perspective, broken-away view of the proximal end of the tibia with a drill guide in place.

Referring first to FIG. 1, a proximal portion of the tibia T is shown in perspective view. A drill guide 10 is positioned against the upper end of the tibia, the drill guide including a block 12 and a manual handle 14 attached to the block. A shank portion 16 extends downwardly from the block at an angle to the handle and is oriented to encounter the tibia distally of the tibial plateau when the block 12 is received against the lateral surface of the tibia as shown in FIG. 1. The block 12 has three bores 17, 18 and 19 extending through it, the thickness of the block being sufficient to appropriately guide a bone drill that is snugly received in the bores. Centrally located bore 18 is used for both right and left knees. For a left knee, as shown in FIG. 1, bore 19 is used to prepare the initial drill hole posterior to bore 18. The face of the drill guide that encounters the surface of the tibia is generally chevron shaped as shown in FIG. 1, so that it can be used with either the left or right tibia.

As will be described in greater detail below, the drill guide 10 is placed against the proximal end of the tibia as shown in FIG. 1, and holes are drilled from the lateral side toward the medial side of the tibia. Posterior and anterior holes 20, 22 are drilled in the tibia as shown, the posterior hole 20 passing entirely through the width of the tibia from its lateral surface to its medial surface and the anterior hole 22 extending only part way through the width of the tibia. A shorter hole 24 is drilled through the bore 21 near the end of the shank 16 and extends inwardly only a short distance through one wall of cortical bone. The position of the hole 20 is of importance: it passes entirely through the tibia from the lateral to the medial surface and preferably angles upwardly slightly from a plane parallel to the plane of the tibial plateau at about a 2° slope. The purpose for the upward angle is to position the apex of the wedge-shaped gap that is formed in a thicker portion of the proximal tibia, the apex being the line of intersection described below and identified in FIG. 7 as 112.

FIG. 8 shows a depth gauge 30 having a thin, elongated rod 32 terminating distally in a hooked end 34, the rod being of a diameter enabling it to easily pass through the hole 20 formed through the proximal tibia. An elongated handle 36 has an interior bore that slidably receives the rod 32, and a lock such as a set screw 38 can he employed to lock the handle to the rod. Once the holes 20, 22 and 24 have been formed, as shown in FIG. 1, the drill guide is removed and the depth gauge 30 is inserted in the hole 20 until the hooked end 34 extends through and hooks over the rim of the hole at the medial surface of the tibia. The handle 36 is then moved distally toward hooked end 34 until the handle contacts the lateral wall of the tibia and the handle is then locked to the rod 32. The distance, then, between the distal end of the handle and the hooked end 34 of the rod presents the width of the proximal tibia adjacent the tibial plateau, as measured through the hole 20. The rod 32 has a predetermined length, and a proximal portion 40 of the rod extends proximally from the handle and terminates in a proximal end 42.

Referring now to FIGS. 6 and 6A, a pin driver is shown generally at 46 and includes a handle 48 and a rod 50 extending from the handle and having an exteriorly threaded end portion 51. The rod terminates distally in a configuration enabling it to couple to the proximal end of a guide pin 64, to be described below. As typified in FIGS. 6 and 6A, the forward end of the rod 50 is configured to have a transversely extending ridge 52 similar to a screwdriver blade. A hollow barrel 54 is interiorly threaded and is threadedly coupled to the rod portion 51. As shown in FIG. 6, as the rod 50 is threaded further into the barrel 54, the transverse ridge 52 at the end of the rod is moved distally toward the distally open end 56 of the barrel. A threaded lock nut 58 is received on the threaded portion 51 of the rod proximal of the barrel, and once the length of the rod within the barrel has been set, the lock nut can be locked down to prevent relative rotation of the rod and barrel.

To set the correct distance that the rod 50 extends within the barrel 54, the proximal end 40 of the depth gauge rod is inserted into the barrel 54 through the open end 56. The rod 50 is threaded into or out of the barrel, as needed, so that the proximal end 44 of the depth gauge handle 36 abuts the open end 56 of the barrel 54 and, simultaneously, the proximal end 42 of the depth gauge rod 32 bottoms out against the ridge 52 of the pin driver rod 50. Lock nut 58 is then locked down against the proximal end of the barrel 54. The depth gauge 30 is removed from the barrel, and is replaced with the calibrated guide pin 64, the proximal end portion 66 of the guide pin 64 being received in the barrel 54. The proximal end 68 of the guide pin 64 is formed to enable it to be rotationally coupled to the pin driver rod 50; in this example, the proximal end 68 is slotted in a manner enabling it to receive the transverse ridge 52 of the pin driver rod 51. The diameter of the shank of the guide pin 64 is such as to enable it to be received snugly within the bore 20 drilled in the tibia, and spaced proximally from the distal end 70 of the guide pin 64 is a threaded portion 72 having threads of a known design adapted to be threaded into bone.

Distal end 70 of the guide pin 64 is introduced into the hole 20, and manual rotation of the pin driver handle 48 threads the guide pin 64 into the hole 20. The threaded portion 72 is set back from distal end 70 to provide a leading section 71 of the guide pin 64 that will align with hole 20 and guide the calibrated guide pin 64 through hole 20 while the guide pin 64 is threaded into the proximal tibia. Once the forward end 56 of the pin driver barrel 54 encounters the lateral surface of the tibia, further rotation of the handle drives the guide pin 64 further into the hole 20 until the slotted proximal end 68 of the guide pin 64 escapes from the ridge 52 of the pin driver rod 51. At this point, the guide pin 64 is appropriately located in the tibia, as shown schematically in FIG. 7, and a saw guide 90 is mounted to the guide pin 64, in a manner now to be described.

Figure 2:
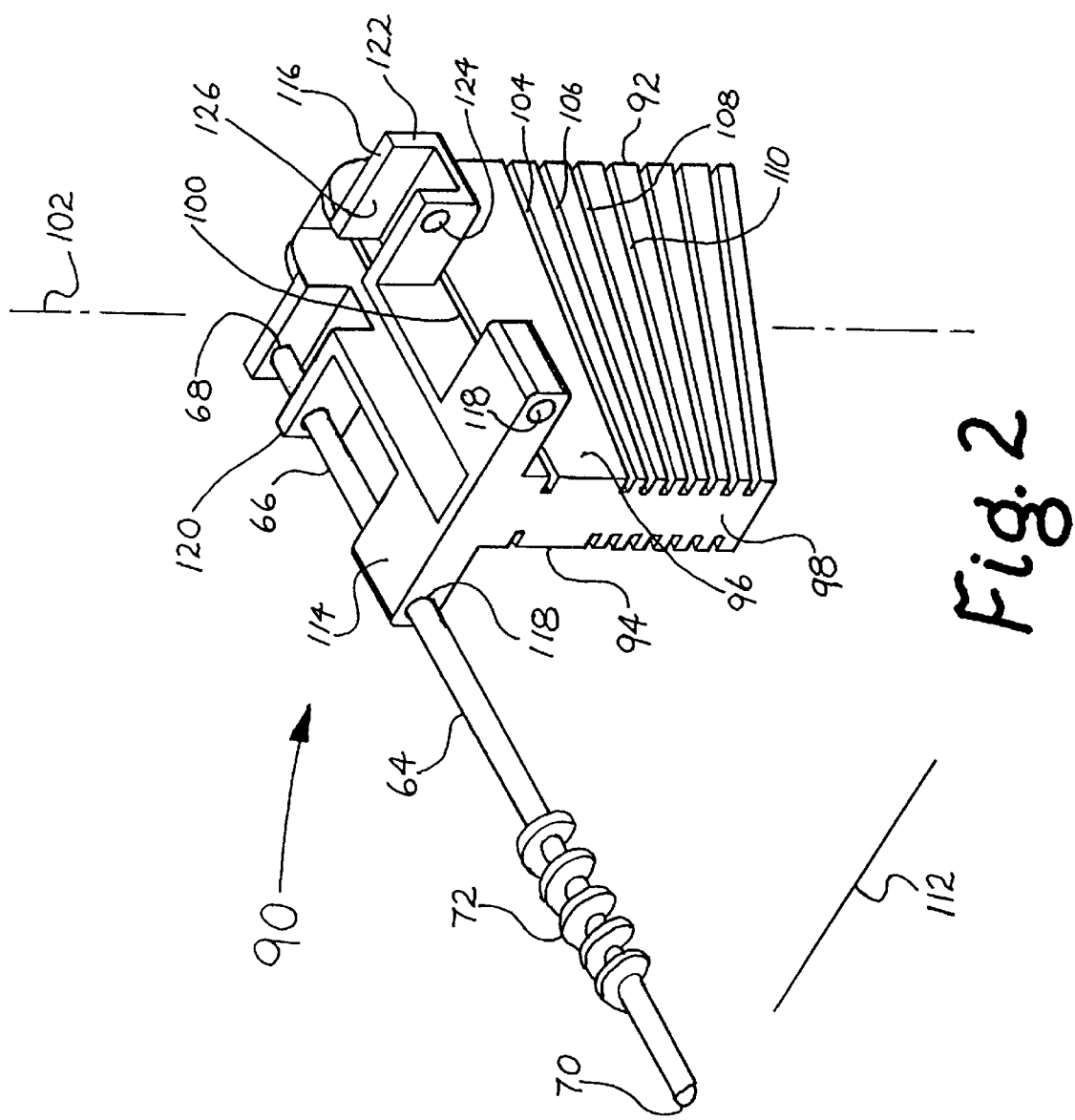
FIG. 2 is a perspective view of a guide body of the invention, with calibrated guide pin in place.
Figure 7:
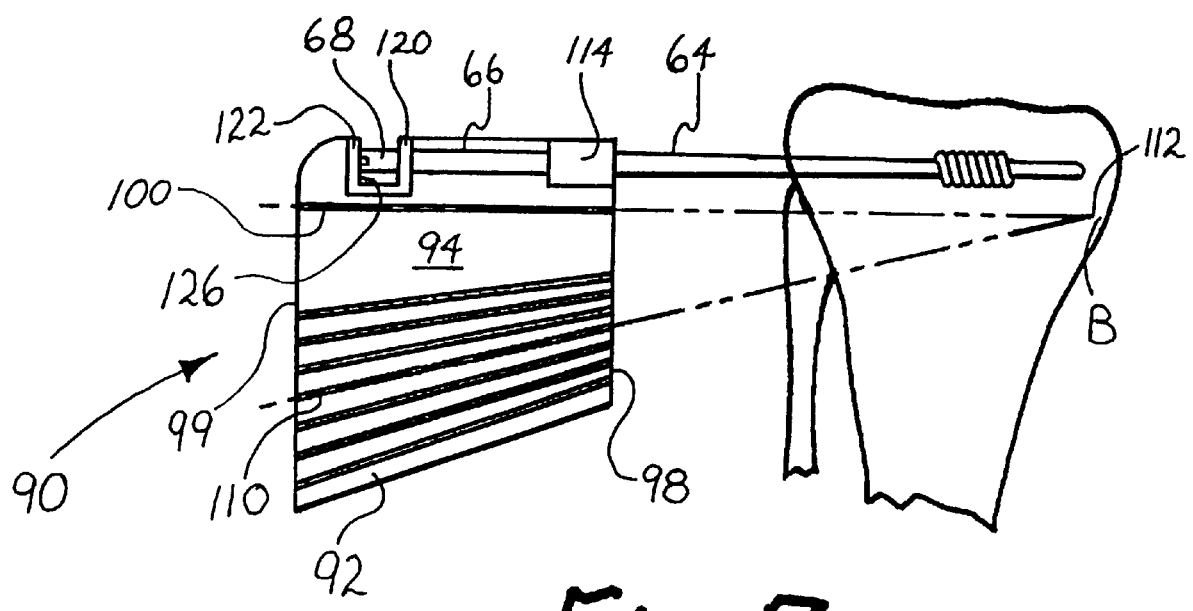
FIG. 7. Is a schematic view showing the guide body and calibrated guide pin in association with the proximal portion of a tibia and showing the planes of planned saw cuts.

FIGS. 2 and 7 show a saw guide generally as 90, the saw guide 90 having a guide body 92 of a generally parallelepiped shape with opposed, spaced side walls 94, 96 and end walls 98, 99, the body having a hollow interior. Slots are formed through the lateral, opposed side stalls 94, 96, the end walls 98, 99 having unslotted portions providing strength and rigidity to the structure. One slot 100 is formed generally perpendicular to the axis 102 of the hollow body 92, and will be employed in the formation of the uppermost osteotomy cut, described below. The other slots 104, 106, 108, 110, etc., extend at different angles to the slot 100. Each slot formed through the side walls 94, 96 defines a plane, and if these planes are extended forwardly (that is, to the left in FIG. 2), they will all intersect in a single line of intersection 112. This line appears as a point 112 in FIG. 7. Saw cuts are then made in the tibia through the use of the saw guides 90, the planes of the cuts intersecting in the predetermined line of intersection and leaving a bone bridge 3 of the desired width. The osteotomy is gradually reduced, causing realignment of the bone, and an L-shaped plate referred to above is installed to secure closure of the osteotomy. At its upper end, the guide body 92 has forward and rearward laterally extending arms 114, 116. Arms 114, nearer the tibia, have through holes 118 sized to closely accommodate the shank of the guide pin 64. Arms 116 each contain two upright flanges 120, 122, the flanges 120 having guide holes 124 similar to holes 118, and the flange 122 having a rearward surface 126 against which may abut the proximal end 68 of the guide pin 64. The guide body 92 preferably is symmetrical, as shown in the drawing, so that it may be used for both right and left knees.

With the guide pin 64 firmly imbedded in the tibia as shown in FIG. 7, the proximal end portion 66 of the guide pin 64 is received through the holes 118, 124 so that the proximal end 68 of the guide pin 64 abuts the surface 124 of the flange 122. In this manner, the exact distance of the saw guide body 92 from the tibia is fixed, which in turn fixes the distance of the line of intersection 112 from the medial surface of the tibia. As will be seen from FIG. 7, movement of the saw guide body 92 to the left or to the right causes a corresponding shift in location of the line of intersection 112. The saw guide body 92 may be held in position rotationally with respect to the guide pin by means of one or more anchor pins (not shown) one of which pins may extend from the tibia through the other of the two holes 118 and permitting the saw guide body freedom of movement toward and away from the tibia but restraining rotational movement of the guide body about the guide pin 64.

With reference to FIG. 8, it will now be understood that the length of the depth gauge handle 36 controls how deeply the proximal portion 40 of the depth gauge 30 will be received within the barrel 54 of the pin driver 46. The depth gauge rod 32 is of predetermined length. Thus, the shorter the length of the handle 36, the greater will be the depth within the barrel 54 to which the proximal end 42 of the depth gauge 30 and hence the proximal end 68 of the guide pin 64 extends, and the shorter will be the length of the guide pin 64 that protrudes from the barrel, such that a shorter length of the guide pin 64 will be threaded into the tibia before the slotted proximal end 68 of the guide pin 64 escapes from the ridge 52. In this manner, the depth to which the distal end 70 of the guide pin 64 is received within the hole 20 formed in the tibia depends upon the length of the handle 36 of the depth gauge 30. The length of the handle, accordingly, may be adjusted so that the width of the bone bridge (shown at "B" in FIG. 7) can be controlled. Handle lengths providing bridge widths of 0.5 mm and 10 mm are contemplated, although various intermediate bone bridge widths may be provided for as well.

With the saw guide body 92 thus supported and positioned with respect to the proximal end of the tibia, appropriate slots in the guide body 92 are chosen so that the resection planes will define the desire wedge angle. One of the slots will be slot 100. For purposes of example, another slot may be slot 110. FIGS. 3 and 4 depict a saw resection guide 130 having an elongated bar portion 132 receivable in a slot of the guide body 92 and a guide block 134 mounted to the blade-shaped bar portion 132. As shown best in FIG. 4, the guide block 134 includes a slot 136 of appropriate width to snuggly accommodate a surgical saw blade, and the block guide block 134 has a forward surface 138 that is curved to accommodate the natural curvature of the lateral surface of the proximal end of the tibia. Several screw holes 140 are formed through the block guide block 134 parallel to the slot 136. The blade portions 132 of two saw resection 130 are received in the respective selected 100, 110, and the guide blocks 134 are secured to the surface of the tibia by small screws. Note that the guide blocks 134 as exemplified in FIG. 4 have portions 142, 144 extending on each side of the slot 136, one portion 142 bearing the holes 140 being thicker than the other portion 144. Desirably, the two saw resection guides 130 are oriented so that the narrower slot defining portions 132, 144 confront each other. The bar portions of the saw resection guides 130 may be locked, if desired, in the guide body. Saw cuts are then carefully made in the tibia through the use of the saw guide slots 136, care being used to limit the depth of each cut to the line of intersection 112. In this manner, the planes of the cuts intersect in the predetermined line of intersection 112 to leave a bone bridge of the desired width. The osteotomy is gradually reduced, causing realignment of the bone, and an L-shaped plate referred to above is installed to secure closure of the osteotomy.

A more detailed version of the surgical protocol involved with use of the present invention follows:

PRE-OPERATIVE PLANNING:

Assess the deformity by means of long film, anterior/posterior (A/P) and lateral X-rays of both extremities with the knees in full extension. Employing the anatomic axis method, mark the anatomic axis of the femur and the tibia on the films and measure the amount of varus or valgus which is present. The osteotomy wedge angle or amount of desired correction is determined by adding the pre-operative varus to the desired postoperative valgus angle (8 degrees of valgus is suggested). If the patient's pre-operative alignment is 2 degrees varus, then a 10 degree correction angle would be required.

Exposure:

After prepping and draping the patient in the usual manner, an inverted L-shaped lateral incision is made to the proximal tibia. The vertical portion of the incision should be midline to the tibia and extend 10 cm distally. The transverse portion should begin just above the tibial tubercle and extend posteriorly to the fibular head. Carry the incision down to periosteum with the lateral portion of the tibia exposed. Disrupt the tibiofibular capsule with an osteotorne or periosteal elevator, or resect the medial portion of the fibular head.

STEP 1:

Place two Keith needles under the lateral meniscus to identify the joint plane and posterior slope of the tibia. Medially the needles will need to be placed percutaneously.

STEP 2:

The drill guide 10 is placed against the Keith needles to establish resection level for the osteotomy. The proximal face of the drill guide is aligned parallel to the Keith needles and to the joint plane. The posterior hole of the drill guide is positioned where the posterior Cancellous Bone Screw is to be placed. An alignment guide (not shown) may be attached to the Drill Guide at this time to aid in placing the initial drill hole. The alignment guide comprises a rod assembly, one end of which is positioned in a drill guide hole and the other end of which indicates the target point for the initial drill hole. The posterior hole is drilled through the medial cortex and an anchor pin placed to secure the Drill Guide. The distal hole of the Drill Guide is centered on the shaft of the tibia. Distally, a hole is drilled through one cortex and the Drill Guide further secured by placing an anchor pin in the drilled hole. Next, the anterior proximal screw hole is drilled through the Drill Guide. This hole should extend to the depth of the tibial tubercle.

STEP 3:

The appropriate depth gauge is selected based on the desired bone bridge width to be preserved. Use of the 0 mm depth gauge will provide a complete resection of the tibial plateau. Use of the 5 mm depth gauge will leave a 5 mm width of bone bridge and use of the 10 mm depth gauge will leave a 10 mm bone bridge. The distal end of the depth gauge is passed through the ⅛" diameter hole and hooked on the ipsilateral cortex. The depth gauge handle is advanced to the lateral bony surface and locked in place.

STEP 4:

The depth gauge is then removed and used to adjust the pin driver by placing the proximal end of the depth gauge in the barrel of the pin driver. The pin driver collar is adjusted such that the proximal end of the depth gauge is bottomed out in the pin driver and the pin driver collar is in contact with the depth gauge handle. The lock nut is then advanced to lock the collar in place. The depth gauge is removed and set aside.

STEP 5:

A calibrated guide pin is placed in the pin driver and threaded into the ⅛" diameter hole prepared in the tibia. The calibrated guide pin is advanced into the proximal tibia until it disengages from the pin driver. The leading section of the calibrated pin aids in placing the pin properly in the pre-drilled hole. The calibrated guide pin is now positioned to ensure the desired bone bridge width.

STEP 6:

The resection blocks are placed into the resection guide body and slider such that the saw blade slot extends anteriorly from the guide body and slider.

STEP 7:

The anterior guide hole of the assembled resection guide is placed over the calibrated guide pin and bottomed out against the pin. The resection guide may be anchored by adding anchor pins in the anterior proximal and distal anchor holes, both of which have been previously drilled, or if the surgeon decides to re-orient the osteotomy, the resection guide may be rotated about the calibrated guide pin to adjust the osteotomy orientation in the sagittal plane. In this case, new drill holes are prepared in the anterior proximal and distal holes of the resection guide body, and anchor pins are appropriately placed.

STEP 8:

With the resection guide properly oriented and both resection blocks advanced to the bony surface, anchor pins may be placed in the resection blocks to secure the resection guide.

STEP 9:

An oscillating saw with a 0.9 mm (0.035") fixed blade 100 mm in length is placed in the saw blade guide slot and the transverse osteotomy is performed, followed by the oblique osteotomy. The proximal resection is made first by placing the saw blade, with depth markings, into the proximal resection slot and advancing the blade until the 100 mm mark aligns with the anterior face of the resection guide body. At this point, the resection is at the proper depth. Next, the distal resection is made in the same fashion, stopping the blade when the 100 mm mark aligns with the anterior face of the resection guide body. Z-retractors are used to protect the soft tissues anteriorly and posteriorly.

STEP 10:

The anchor pins, resection guide and calibrated guide pin are removed and the wedge of bone excised.

STEP 11:

The L-shaped high tibial osteotomy ("HTO") plate is positioned with the top of the plate parallel to the osteotomy line. The depth gauge is used to determine the appropriate length of screws and 6.5 mm cancellous screws are inserted proximally. The screws should not he tightened down fully until the distal screws have been applied.

STEP 12:

One post of the compression clamp is fitted into the distal anchor hole and the other end in engaged in the distal most hole of the plate. Reduce the osteotomy site using the compression clamp. Slow compression should he applied and frequently takes up to 5–10 minutes.

STEP 13:

Evaluate the overall alignment using a bovie cord or alignment rod from the center of the femoral head to the center of the ankle.

STEP 14:

While maintaining compression, drill and tap through the round central hole of the plate. Use the depth gauge to determine the proper screw length and insert a 4.5 mm cortical screw. Remove the compression device and drill, tap and insert a 4.5 mm screw into the distal hole. Tighten the proximal cancellous screws.

STEP 15:

Insert a drain along the tibia and close the would in layers. Close the subcutaneous tissue and apply a large compressive dressing.

NOTE: It is recommended that in younger patients the hardware be removed after complete union of the osteotomy (usually 6 to 12 months).

While a preferred embodiment of the present invention has been described, it should be understood that various changes, adaptations, and modifications may be made without departing from the spirit of the invention.

What is claimed is:

1. A wedge osteotomy apparatus for performing a nearly complete subarticular wedge resection of a bone, the apparatus comprising an osteotomy guide having a guide body provided with a series of slots, a pair of saw guide resection blocks each including a bar portion receivable in one of said slots and having a slotted block portion adapted to guide a saw blade in a sawing plane during a bone cutting procedure, the slots in the guide block being so arranged as to locate said resection blocks so that the sawing planes intersect each other at a line of intersection, measuring means for fixing the desired position of the line of intersection within the bone and with respect to a surface of the bone, and means responsive to said measuring means for spacing the guide body a predetermined distance from the tibia to appropriately position said line of intersection.

2. A wedge osteotomy device for cutting a wedge from a bone, the device comprising:

measuring means for determining the distance to a far side cortical wall of the bone and defining a line of intersection within the bone, at or near the far side cortical wall;

a calibrated guide pin and means, responsive to the measuring means, for inserting the calibrated guide pin into the bone a predetermined distance from the defined line of intersection;

a guide body, telescopically engageable with the calibrated guide pin and positionable with respect to a near cortical wall of the bone, having at least two guide slots, the at least two guide slots each defining at least two resection planes that are at defined angles to each other such that all resection planes of the at least two resection planes intersect at the defined line of intersection; and resection means, engageable with the at least two guide slots, for resecting the bone in two resection planes as a wedge of the bone having one apex at the defined line of intersection.

3. The device of claim 2 wherein the measuring means includes means for drilling a hole through the bone and a depth gauge having a predetermined length for passing through the hole.

4. The device of claim 3 wherein the depth gauge includes a hook at one end for engaging the far cortical wall of bone and a handle having a predetermined length, slidably engageable along the depth gauge and abuttable to the near cortical wall of bone.

5. The device of claim 2 wherein the means for inserting includes a pin driver operably engageable with an end of the calibrated guide pin and having an adjustable collar along the length of the long axis of the pin driver.

6. The device of claim 2 wherein the resection means includes at least one resection block, the at least one resection block including a bar portion detachably receivable in one of the at least two guide slots, and a slotted portion adapted to guide a saw blade in the resection plane of the guide slot such that the edge of the saw blade reaches the defined line of intersection.

* * * * *